United States Patent
Kuhara

(10) Patent No.: US 9,594,138 B2
(45) Date of Patent: Mar. 14, 2017

(54) MAGNETIC RESONANCE IMAGING APPARATUS AND MAGNETIC RESONANCE IMAGING METHOD

(75) Inventor: Shigehide Kuhara, Otawara (JP)

(73) Assignee: TOSHIBA MEDICAL SYSTEMS CORPORATION, Otawara-Shi, Tochigi-Ken (JP)

(*) Notice: Subject to any disclaimer, the term of this patent is extended or adjusted under 35 U.S.C. 154(b) by 1403 days.

(21) Appl. No.: 13/417,585

(22) Filed: Mar. 12, 2012

(65) Prior Publication Data
US 2012/0161760 A1    Jun. 28, 2012

Related U.S. Application Data

(63) Continuation of application No. PCT/JP2011/074594, filed on Oct. 25, 2011.

(30) Foreign Application Priority Data

Nov. 4, 2010   (JP) ................. 2010-247507

(51) Int. Cl.
*G01R 33/56* (2006.01)
*A61B 5/055* (2006.01)
*A61B 5/00* (2006.01)

(52) U.S. Cl.
CPC ........ *G01R 33/5602* (2013.01); *A61B 5/0037* (2013.01); *A61B 5/055* (2013.01); *A61B 2576/023* (2013.01)

(58) Field of Classification Search
CPC ... G01R 33/5602; A61B 5/055; A61B 5/0037; A61B 2576/023
See application file for complete search history.

(56) References Cited

U.S. PATENT DOCUMENTS

| | | | |
|---|---|---|---|
| 6,781,375 B2 | 8/2004 | Miyazaki et al. | |
| 7,965,079 B2 * | 6/2011 | Furudate | G01F 1/56 324/306 |
| 8,060,180 B2 * | 11/2011 | Pai | G01R 33/563 324/307 |

(Continued)

FOREIGN PATENT DOCUMENTS

| | | |
|---|---|---|
| JP | A 2001-299724 | 10/2001 |
| JP | 2004-24637 | 1/2004 |

(Continued)

OTHER PUBLICATIONS

Office Action issued Jan. 6, 2014, in CN Patent Application No. 201180002478.2.

(Continued)

*Primary Examiner* — Dixomara Vargas
(74) *Attorney, Agent, or Firm* — Nixon & Vanderhye P.C.

(57) ABSTRACT

A magnetic resonance imaging apparatus according to an embodiment includes a calculation unit and an imaging unit. The calculation unit calculates an inversion time for imaging by analyzing frames of image data or magnetic resonance signals acquired from an object. The frames of the image data or the magnetic resonance signals are acquired in response to inversion times which are different with each other and set based on a inversion recovery method. The imaging unit performs the imaging under the inversion recovery method using the inversion time calculated for the imaging.

11 Claims, 6 Drawing Sheets

(56) References Cited

U.S. PATENT DOCUMENTS

| | | | | |
|---|---|---|---|---|
| 8,085,040 | B2* | 12/2011 | Yamada | A61B 5/0263 324/306 |
| 8,269,495 | B2* | 9/2012 | Littmann | A61B 5/055 324/309 |
| 8,515,526 | B2* | 8/2013 | Miyazaki | A61B 5/055 600/410 |
| 8,571,288 | B2* | 10/2013 | Sugiura | A61B 5/055 345/530 |
| 8,848,990 | B2* | 9/2014 | Xue | G06T 7/0024 382/128 |
| 9,002,430 | B2* | 4/2015 | Riederer | G01R 33/4818 600/419 |
| 9,129,424 | B2* | 9/2015 | Xue | G06T 11/003 |
| 9,183,626 | B2* | 11/2015 | Zhao | G06T 7/0012 |
| 9,488,711 | B2* | 11/2016 | Kimura | G01R 33/5635 |
| 2010/0085051 | A1 | 4/2010 | Littmann et al. | |
| 2010/0191099 | A1 | 7/2010 | Salerno et al. | |

FOREIGN PATENT DOCUMENTS

| | | |
|---|---|---|
| JP | 2004-305454 | 11/2004 |
| JP | A 2006-149563 | 6/2006 |
| JP | 2007-312966 | 12/2007 |

OTHER PUBLICATIONS

Office Action issued May 12, 2015 in JP Patent Application No. 2011-234436.
Office Action issued May 26, 2015 in CN Patent Application No. 201180002478.2.
Notification of Transmittal of Translation of the International Preliminary Report on Patentability in PCT/JP2011/074594 mailed May 23, 2013.
International Search Report for PCT/JP2011/074594, mailed Dec. 27, 2011.
Office Action issued Sep. 28, 2014, in CN Patent Application No. 201180002478.2.

* cited by examiner

MAGNETIC RESONANCE IMAGING APPARATUS AND MAGNETIC RESONANCE IMAGING METHOD

CROSS REFERENCE

This is a continuation of Application PCT/JP2011/74594, filed Oct. 25, 2011.

This application is based upon and claims the benefit of priority from Japanese Patent Application No. 2010-247507, filed Nov. 4, 2010; the entire contents of which are incorporated herein by reference.

FIELD

Embodiments described herein relate generally to a MRI (magnetic resonance imaging) apparatus and a magnetic resonance imaging method.

BACKGROUND

MRI is an imaging method which excites nuclear spins of an object placed in a static magnetic field and magnetically excited with a RF (radio frequency) signal having the Larmor frequency and reconstructs an image based on MR (magnetic resonance) signals generated due to the excitation.

As a morphological imaging method of the heart using MRI, a delayed enhancement (DE: Delayed Enhancement or LGE: Late Gadolinium Enhancement) imaging method is known. This delayed enhancement imaging method is an imaging method of performing imaging of an object at a time when a predetermined time has elapsed after injecting a contrast agent into the object.

In the delayed enhancement imaging for the heart, a 180-degree inversion recovery (IR: inversion recovery) pulse is applied prior to acquiring MR data for imaging, which pulse is for inverting the longitudinal magnetization Mz in the heart under the static magnetic field so that the longitudinal magnetization becomes a negative value. And, after applying the IR pulse, imaging data is acquired at a time when the longitudinal magnetization at the myocardium returns to almost zero due to the longitudinal relaxation (T1 relaxation). A period of time ranging from the application time of the IR pulse to application of an 90-degree RF pulse applied for acquiring the imaging data is called an inversion time (TI: inversion time). In other words, the TI is decided to allow the longitudinal magnetization at the myocardium to be zero, resulting in suppression of signals from the tissue of the myocardium.

Further, in the delayed enhancement imaging for the heart, in cases where a contrast agent administered into an object being diagnosed flows into its normal myocardium, the contrast agent is washed out from the myocardium approximately within a span of 10 to 15 minutes after the administration. Hence, after an elapse of 10 to 15 minutes from the administration of the constant agent, there remains only a small residual amount of the contrast agent in the normal myocardial tissue. In contrast, when the contrast agent flows into lesions such as areas of cardiac infarction, the contrast agent cannot be washed out even after an elapse of 10 to 15 minutes, and still remains in the myocardial tissue.

Meanwhile, the longitudinal relaxation time (T1) of spins in an area of cardiac infarction becomes shorter than T1 in the normal myocardial tissue due to effects of the contrast agent. Hence, when the inversion time TI is set such that imaging data is acquired after an elapse of 10 to 15 minutes from the administration of the contrast agent, the intensity of MR signals acquired from the area of cardiac infarction in which the longitudinal magnetization of spins has recovered so as to show a positive value becomes larger than the intensity of MR signals acquired from the normal myocardium. Particularly, when the TI is set to allow imaging data to be acquired at a time when the longitudinal magnetization becomes almost zero, the intensity of MR signals acquired from the normal myocardium is almost zero so that the area of cardiac infarction can be clearly depicted as higher-intensity parts.

Hence, in order to obtain a clear contrast between the normal myocardium and the area of cardiac infarction, it is essential to accurately obtain a TI that makes the myocardium have a cardiac magnetization of zero at a time when imaging data is acquired.

In view of this respect, a TI-Prep method is proposed, in which a pre-scan is performed prior to an imaging scan to acquire a plurality of frames of image data with the TI changed to different amounts, and a proper TI is obtained based on a plurality of images acquired through the pre-scan and produced in response to the different TIs. In performing the TI-Prep method, a plurality of images corresponding to the different TIs are displayed to make a user select, through a user's visual check, an image having the lowest signal intensity at the myocardium. This enables acquisition of a proper TI. That is, the TI with which the image having the lowest signal intensity at the myocardium is acquired corresponds to a proper TI.

As represented by the delayed enhancement imaging for the heart, in imaging using the IR method, it is essential to set the TI with precision. In particular, in the IR imaging performed with the use of the absolute-value image signals, optimally setting the TI is an important issue, because signals are sampled discretely but a minimum value of signals is theoretically at one point. It is further desired to properly set the TI in imaging in order for obtaining more useful diagnosis aid information.

An object of the present disclosure is to a magnetic resonance imaging apparatus and a magnetic resonance imaging method which can obtain useful diagnostic information from portions being imaged, including the heart, by imaging based on an IR method which uses a properly set TI.

PRIOR TECHNICAL LITERATURE

[Patent literature 1] JPA 2004-24637

BRIEF DESCRIPTIONS OF DRAWINGS

DETAILED DESCRIPTION

In general, according to one embodiment, a magnetic resonance imaging apparatus includes a calculation unit and an imaging unit. The calculation unit calculates an inversion time for imaging by analyzing frames of image data or magnetic resonance signals acquired from an object. The frames of the image data or the magnetic resonance signals are acquired in response to inversion times which are different with each other and set based on a inversion recovery method. The imaging unit performs the imaging under the inversion recovery method using the inversion time calculated for the imaging.

Further, according to another embodiment, a magnetic resonance imaging unit includes a calculation unit and a substance specifying unit. The calculation unit calculates a formula of a curve obtained by curve fitting applied to frames of image data or magnetic resonance signals acquired responsively to inversion times which are different with each other and set based on a recovery method. The substance specifying unit enables a display unit to display at least one of a T1 value obtained through the curve fitting, the inversion time given when the curve becomes zero, a shape of the curve, and information indicating a substance estimated based on the T1 value.

Still further, according to another embodiment, a magnetic resonance imaging method includes calculating an inversion time for imaging by analyzing frames of image data or magnetic resonance signals acquired from an object and performing the imaging under the inversion recovery method using the inversion time calculated for the imaging. The frames of the image data or the magnetic resonance signals are acquired in response to inversion times which are different with each other and set based on a inversion recovery method.

A magnetic resonance imaging apparatus and a magnetic resonance imaging method according to embodiments of the present invention will now be described with reference to the accompanying drawings.

First Embodiment

Figure 1:
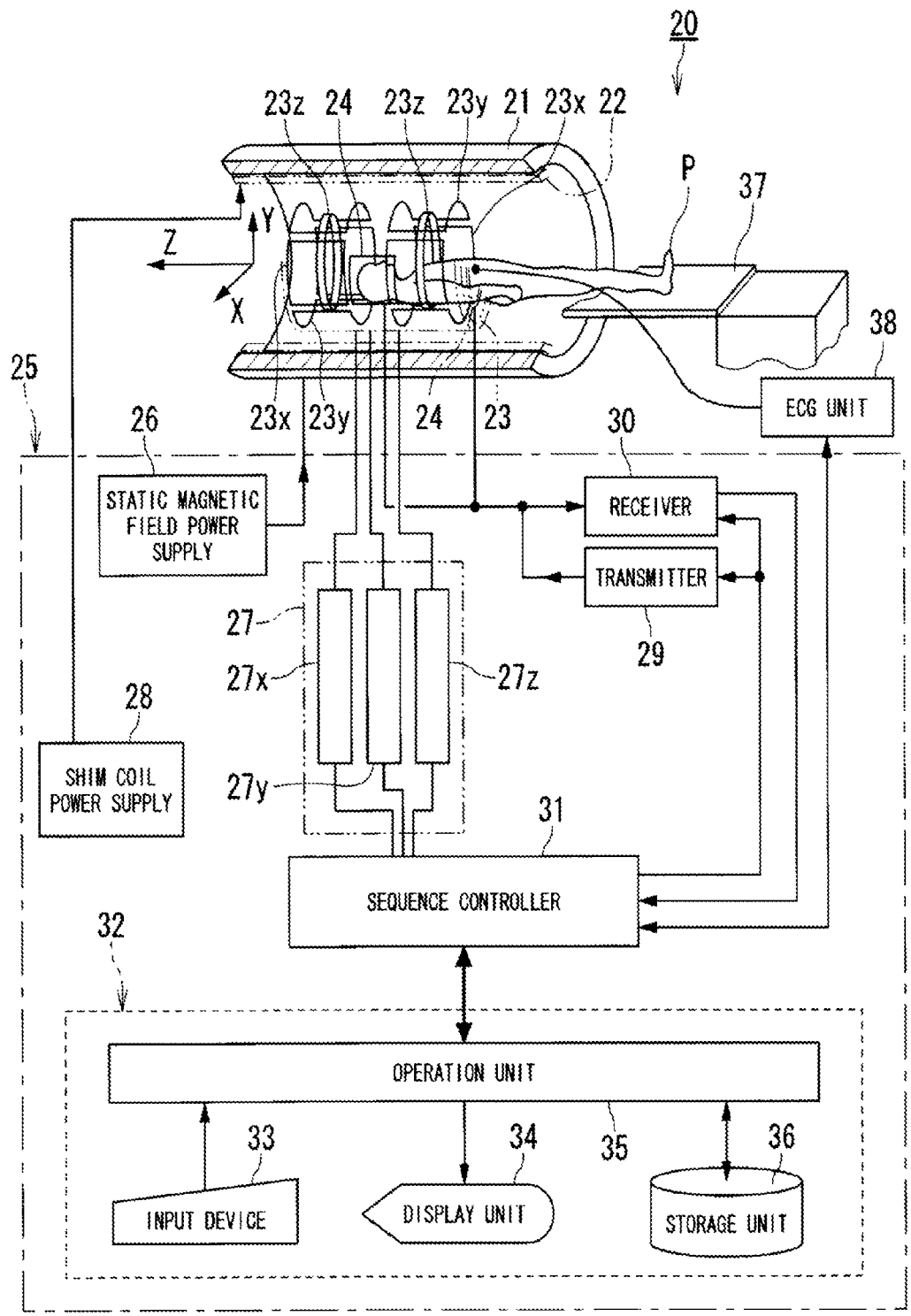
FIG. 1 is a block diagram showing a magnetic resonance imaging apparatus according to the first embodiment of the present invention.

FIG. 1 is a block diagram showing a magnetic resonance imaging apparatus according to the first embodiment of the present invention.

A magnetic resonance imaging apparatus 20 includes a static field magnet 21 for generating a static magnetic field, a shim coil 22 arranged inside the static field magnet 21 which is cylinder-shaped, a gradient coil 23 and RF coils 24.

The magnetic resonance imaging apparatus 20 also includes a control system 25. The control system 25 includes a static magnetic field power supply 26, a gradient power supply 27, a shim coil power supply 28, a transmitter 29, a receiver 30, a sequence controller 31 and a computer 32. The gradient power supply 27 of the control system 25 includes an X-axis gradient power supply 27x, a Y-axis gradient power supply 27y and a Z-axis gradient power supply 27z. The computer 32 includes an input device 33, a display unit 34, an operation unit 35 and a storage unit 36.

The static field magnet 21 communicates with the static magnetic field power supply 26. The static magnetic field power supply 26 supplies electric current to the static field magnet 21 to generate a static magnetic field in an imaging region. The static field magnet 21 includes a superconductivity coil in many embodiments. The static field magnet 21 gets electric current from the static magnetic field power supply 26 which communicates with the static field magnet 21 at excitation. However, once excitation has been performed, the static field magnet 21 is usually isolated from the static magnetic field power supply 26. The static field magnet 21 may include a permanent magnet which makes the static magnetic field power supply 26 unnecessary.

The static field magnet 21 has the cylinder-shaped shim coil 22 coaxially inside itself. The shim coil 22 communicates with the shim coil power supply 28. The shim coil power supply 28 supplies current to the shim coil 22 so that the static magnetic field becomes uniform.

The gradient coil 23 includes an X-axis gradient coil 23x, a Y-axis gradient coil 23y and a Z-axis gradient coil 23z. Each of the X-axis gradient coil 23x, the Y-axis gradient coil 23y and the Z-axis gradient coil 23z which is cylinder-shaped is arranged inside the static field magnet 21. The gradient coil 23 has also a bed 37 in the area formed inside it which is an imaging area. The bed 37 supports an object P. The RF coils 24 include a whole body coil (WBC), which is built in the gantry, for transmission and reception of RF signals and local coils, which are arranged around the bed 37 or the object P, for reception of RF signals.

The gradient coil 23 communicates with the gradient power supply 27. The X-axis gradient coil 23x, the Y-axis gradient coil 23y and the Z-axis gradient coil 23z of the gradient coil 23 communicate with the X-axis gradient power supply 27x, the Y-axis gradient power supply 27y and the Z-axis gradient power supply 27z of the gradient power supply 27 respectively.

Electric currents are thus supplied from the X-axis gradient power supply 27x, the Y-axis gradient power supply 27y and the Z-axis gradient power supply 27z to the X-axis gradient coil 23x, the Y-axis gradient coil 23y and the Z-axis gradient coil 23z, respectively, whereby the electric currents produce an X-axis gradient magnetic field Gx, a Y-axis gradient magnetic field Gy and a Z-axis gradient magnetic field Gz are generated.

The RF coils 24 communicate with at least one of the transmitter 29 and the receiver 30. The transmission RF coil 24 has a function to transmit an RF signal given from the transmitter 29 to the object P. The reception RF coil 24 has a function to receive a MR signal generated due to nuclear spins inside the object P which are excited by the RF signal to give to the receiver 30.

The sequence controller 31 of the control system 25 communicates with the gradient power supply 27, the transmitter 29 and the receiver 30. The sequence controller 31 has a function to store sequence information describing control information needed in order to make the gradient power supply 27, the transmitter 29 and the receiver 30 drive and generate gradient magnetic fields Gx, Gy and Gz in the X, Y and Z directions and a RF signal by driving the gradient power supply 27, the transmitter 29 and the receiver 30 according to a predetermined sequence stored. The control information above-described includes motion control information, such as intensity, application period and application timing of the pulse electric current which should be applied to the gradient power supply 27.

The sequence controller 31 is also configured to give raw data to the computer 32. The raw data is complex data obtained through the detection of a MR signal and A/D (analog to digital) conversion to the MR signal detected in the receiver 30.

The transmitter 29 has a function to provide an a RF signal to the RF coil 24 in accordance with control information provided from the sequence controller 31. The receiver 30 has a function to generate raw data which is digitized complex number data by detecting a MR signal provided by the RF coil 24 and performing predetermined signal processing and A/D converting to the MR signal detected. The receiver 30 also has a function to provide the generated raw data to the sequence controller 31.

Further, the magnetic resonance imaging apparatus 20 is provided with an ECG unit 38 which acquires an ECG (electro cardiogram) signal from the object P. The circuitry is configured such that the ECG signal, which is acquired by the ECG unit 38, is sent to the computer 32 via the sequence control 31.

Instead of using the ECG signal indicating object's heartbeats which serves as the heart rate information, it is possible to detect a peripheral pulse gating (PPG) signal also indicating object's heartbeats which serves as the pulse wave information. The PPG signal is detected from, for example, from a fingertip as an optical signal corresponding to the pulse wave appearing in the fingertip. To acquire this PPG signal, a PPG signal detection unit is used. In the present embodiment, a configuration in which the ECG signal is acquired will be described.

When the operation unit 35 executes programs stored in the storage unit 36 of the computer 32, the computer 32 is given various functions. Incidentally, at least part of the programs can be replaced by electric circuits assigned to various specified functions in the magnetic resonance imaging apparatus 20.

Figure 2:
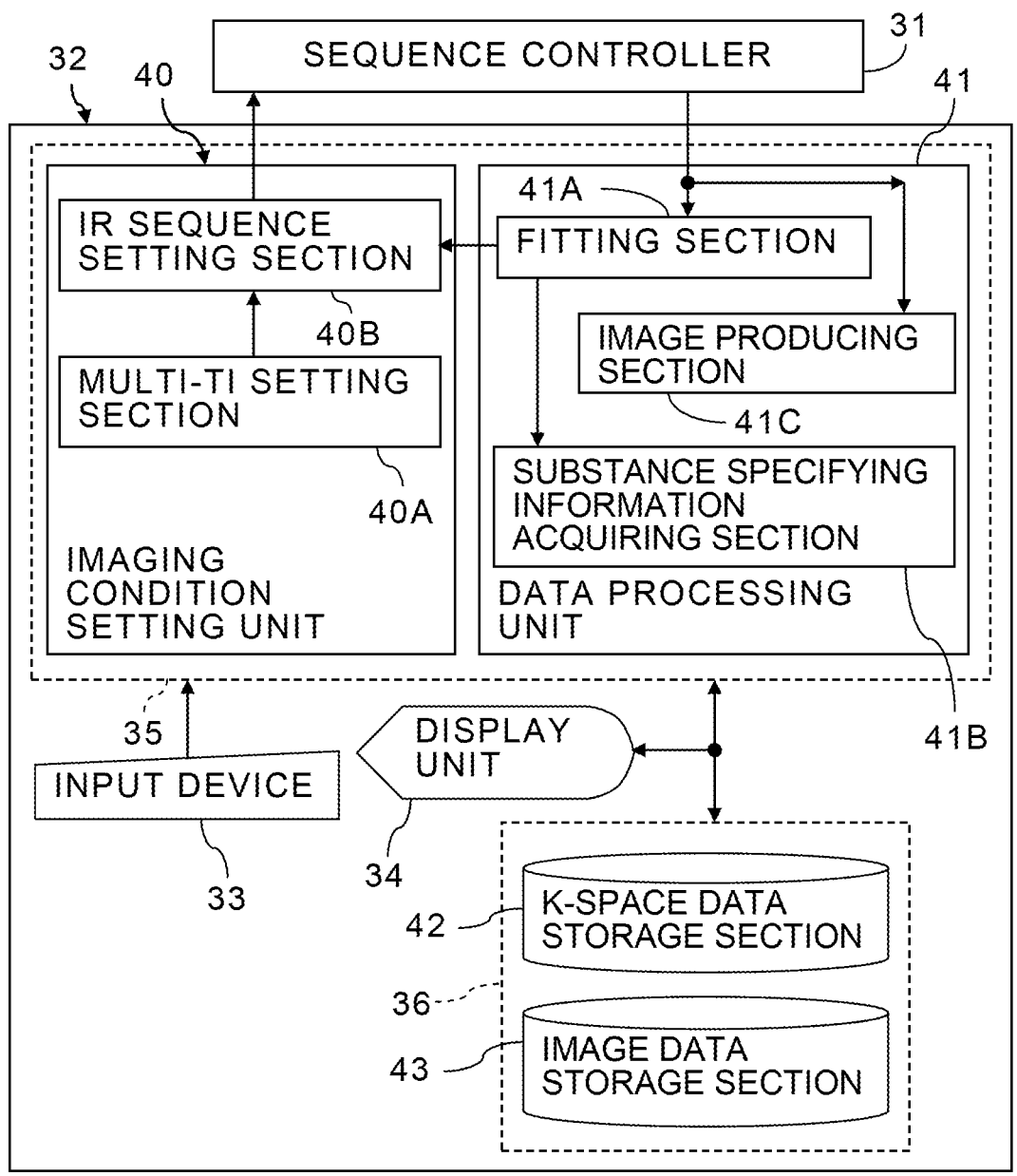
FIG. 2 is a functional block diagram of a computer shown in FIG. 1.

FIG. 2 is a functional block diagram of the computer 32 shown in FIG. 1.

The operation unit 35 of the computer 32 functions as an imaging condition setting unit 40 and a data processing unit 41 by executing programs stored in the storage unit 36. The storage unit 36 functions as a k-space data storage section 42 and an image data storage section 43. The imaging condition setting unit 40 includes a multi-TI setting section 40A and an IR sequence setting section 40B. The data processing unit 41 includes a fitting section 41A, a substance specifying information acquiring section 41B, and an image producing section 41C.

The imaging condition setting unit 40 has functions of setting imaging conditions including an IR sequence for imaging based on the IR method and outputting to the sequence controller 31 the imaging conditions which has been set. Especially, the imaging condition setting unit 40 has a function of setting, in addition to an imaging condition for an imaging scan, a data acquiring condition for a pre-scan performed prior to the imaging scan to decide an impression timing of the IR pulse.

The data acquiring condition for the pre-scan is set to acquire MR data necessary for producing a plurality of frames of image data, during which acquisition the MR data are acquired as an TI from an impression time of a 180-degreee IR pulse to an impression time of a α-degree RF pulse for acquiring MR data in the IR sequence is changed to various amounts.

In imaging objects involving motions or displacements caused by the heartbeats as can be seen in imaging the heart or blood flows, data are acquired in synchronization with the ECG signal detected by the ECG unit 38. However, such a synchronization technique is not necessary for fluid and organs with no periodicity in their motion, which are for example cerebrospinal fluid (CSF) and peripheral blood flows.

On the other hand, the imaging condition for the imaging scan includes an IR sequence with a TI which enables a portion of interest to be depicted with higher intensity signals but signals from other portions to be suppressed in intensity. For example, in the delayed enhancement imaging for the heart, the IR sequence is set to have a TI which allows signals from the normal myocardial tissue to be suppressed in intensity such that an area of cardiac infarction is depicted with higher intensity signals. Further, in the non-enhancement blood flow imaging, the IR sequence is set to have a TI which causes signals from a background behind blood flow portions to be suppressed in intensity such that the blood flow portions are depicted as higher intensity signal portions.

In the present embodiment, based on data acquired by a pre-scan, a proper TI for the imaging scan is decided by the data processing unit 41 which will be described later.

The present embodiment exemplifies a case where the delayed enhancement imaging for the heart is executed with the ECG gating in order to suppress the intensity of signals from the normal myocardial tissue so that an area of cardiac infarction is depicted with higher-intensity signals.

The multi-TI setting section 40A has a function of setting mutually different plural TIs to set an IR sequence for the pre-scan.

The IR sequence setting section 40B has a function of setting the IR sequence for the pre-scan using the plural TIs which are set by the multi-TI setting section 40A, and another function of setting the IR sequence for the imaging scan using a TI calculated by the fitting section 41A.

Figure 3:
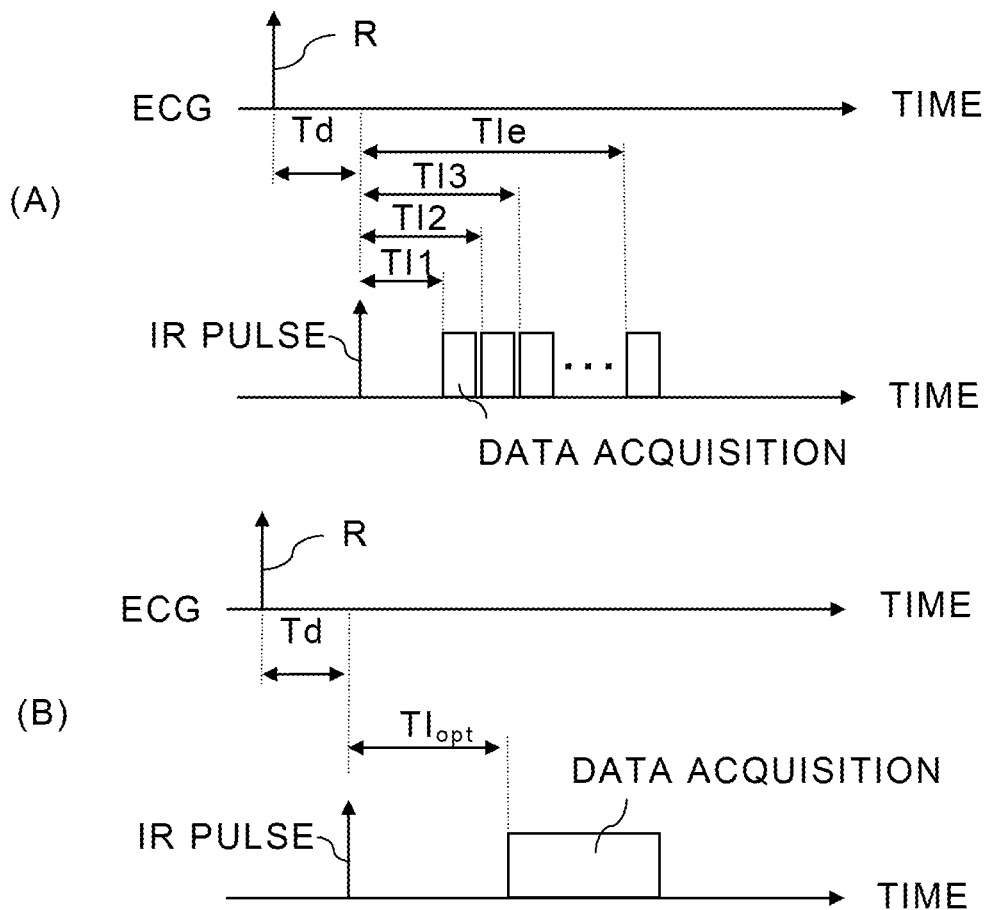
FIG. 3 is a timing chart showing an IR sequence for the pre-scan and an IR sequence for the imaging scan, which are set in the imaging condition setting unit shown in FIG. 2.

FIG. 3 is a timing chart showing an IR sequence for the pre-scan and an IR sequence for the imaging scan, which are set in the imaging condition setting unit 30 shown in FIG. 2.

In FIG. 3, the horizontal axes show time and a reference shows an ECG signal. (A) of FIG. 3 shows the IR sequence for the pre-scan, while (B) of FIG. 3 shows the IR sequence for the imaging scan.

As shown in (A) of FIG. 3, according to an imaging condition which is set for the pre-scan, a 180-degree IR pulse is first applied at a time when a predetermined delay time (Td) elapses after an R-wave which serves as one of reference waves of the ECG signal. Then, IR sequences for acquiring MR data are applied respectively at time instants when different inversion times TIs (T1, T2, T3, . . . , Te) elapse from the application time of the 180-degree IR pulse.

In order to shorten the data acquisition time, the pre-scan can be set to acquire data to be mapped in an image matrix which is less in number than an image matrix desired by an imaging scan. Furthermore, even if a three-dimensional (3D) imaging scan is desired, the IR sequence for the pre-scan can be set so as to acquire data from a single slice or a few slices. In this case, to prevent the TI from changing due to changes of conditions such as image matrix sizes, it is preferred that data being mapped in a central area of the k-space be first acquired, because the central area has a larger influence on the contrast of an image.

Alternatively, in (A) of FIG. 3, a plurality of sets of MR data which respond to the mutually different TIs may be overlapped in time when being acquired. In other words, common MR signals may be used as the plurality of sets of MR data responding to the mutually different TIs. Hence, in this case, the time necessary for executing the pre-scan can be shortened.

In contrast, without acquiring the plurality of sets of MR data at different time instants after the common 180-degree IR pulse as shown in (A) of FIG. 3, a combination of applying the 180-degree IR pulse and acquiring MR data in response to each of the different TIs may be repeated. That is, in such a case, a plurality of 180-degree IR pulses whose TIs differ from each other are applied in sequence.

Meanwhile, as shown (B) of FIG. 3, according to an imaging condition which is set for the imaging scan, a 180-degree IR pulse is first applied at a time when a predetermined delay time (Td) elapses after an R-wave of the ECG signal. Then, IR sequences for acquiring data are applied at a time instant when an optimum $TI_{opt}$ elapses from the application time of the 180-degree IR pulse. The optimum $TI_{opt}$ is calculated by the fitting section 41A.

The data processing unit 41 has several functions. One function is to obtain MR data outputted from the sequence controller 31 to map the obtained MR data, as k-space data, in the k-space produced in the k-space data storage section 42. Another function is to apply data processing to data acquired by both the pre-scan and the imaging scan so as to produce image data, and write the produced image data into the image data storage section 43. Another function is to calculate an optimum $TI_{opt}$ for the imaging by analyzing the plurality of sets of image data of the object P, which respond to the mutually different plural TIs during the pre-scan executed under the IR technique. Still another function is to display, on the display unit 34, image data read from the image data storage section 43.

The fitting section 41A also has several functions, one of which is to obtain from the image data storage section 43 image data acquired by the pre-scan in response to the mutually different plural TI (T1, T2, T3, . . . , Te), and apply a fitting curve to image data in a single ROI (region of interest) or plural ROIs such that an intensity change curve of an image signal in the myocardial tissue is calculated in relation to changes in the TIs. Another function of the fitting section is to use the change curve of signal intensities vs. changes in the TIs which is calculated every ROI so that a TI specified at a signal intensity of zero is provided to the IR sequence setting section 40B as the foregoing optimum $TI_{opt}$ for the imaging scan.

Figure 4:
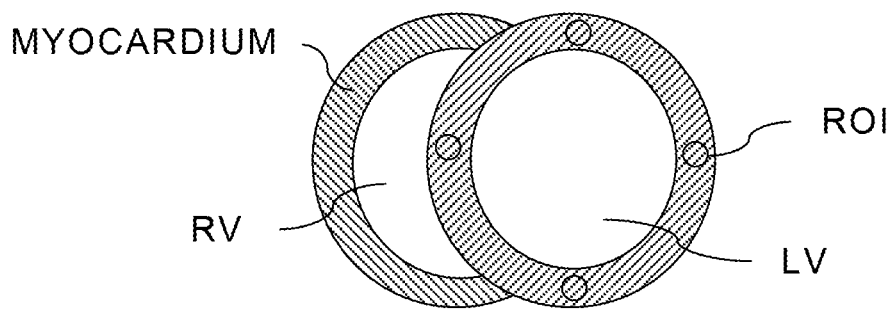
FIG. 4 is a view exemplifying ROIs which are set by the data processing unit shown in FIG. 2.

FIG. 4 is a view exemplifying ROIs which are set by the data processing unit 41 shown in FIG. 2.

When the fitting section 41A reconstructs MR data acquired by the pre-scan, morphological image data showing a desired section of the heart are produced every TI as shown in FIG. 4. FIG. 4 exemplifies minor-axis image data of the heart produced in response to one TI. A minor-axis section of the heart provides a structure having the left ventricle and the right ventricle both sectioned by the myocardium.

A user refers to minor-axis images of the heart displayed on the display unit 34, during which reference the user is able to manipulate the input device 33 to place a single or plural ROIs at desired positions on section images of the myocardium. From a standpoint of obtaining an accurate $TI_{opt}$ for the imaging scan, it is desired to raise the number of ROIs. FIG. 4 shows an example in which four ROIs are placed.

The fitting section 41A then produces, for every ROI, a curve showing changes in the image signal intensities in the myocardial tissue depending on changes in the TI. Further, the fitting section uses the plural curves resultant from the plural ROIs to decide a TI for the imaging scan.

Figure 5:
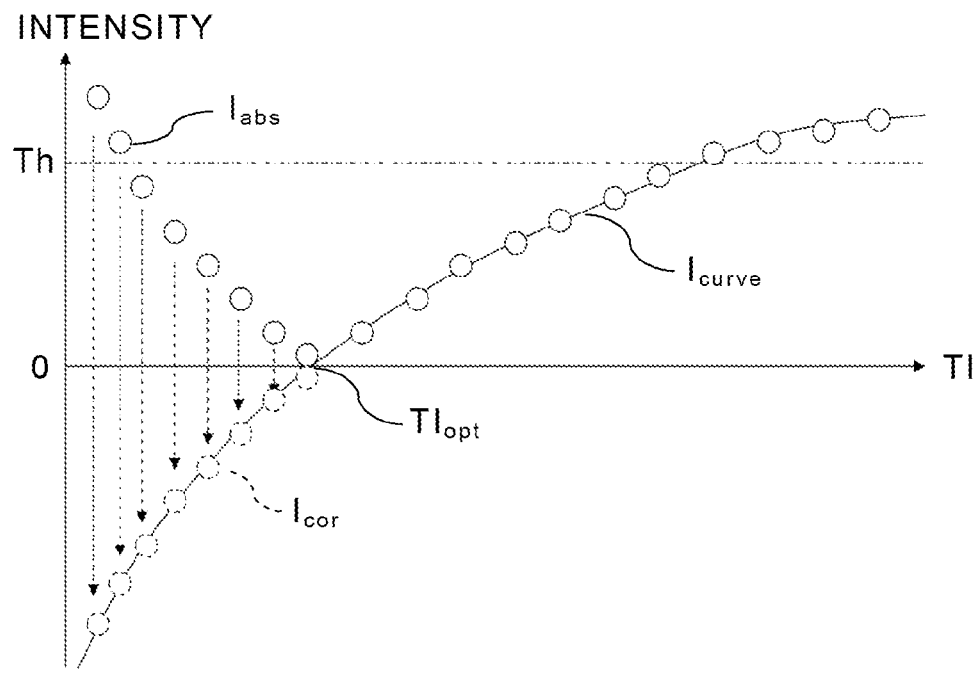
FIG. 5 is a graph explaining how to decide a $TI_{opt}$ for the imaging scan, which is performed by the data processing unit shown in FIG. 2.

FIG. 5 is a graph explaining the first decision technique for obtaining the $TI_{opt}$ for the imaging scan, which is performed by the data processing unit 41 shown in FIG. 2.

The graph in FIG. 5 has a vertical axis showing intensity of an image signal and a horizontal axis showing the TIs. By plotting a signal intensity every TI, which is obtained in a ROI in each of the plurality of sets of imaged data acquired through the pre-scan, discrete plotted data $I_{abs}$ are produced as shown by a solid line marking. Incidentally the signal intensity in each ROI can be a representative value such as an average over plural pixel values in each ROI or a maximum value of the pixel values in each ROI.

In the IR imaging, absolute values of complex image signals each consisting of a real part and an imaginary part are usually used as image data for display. Additionally, MR signals used for producing image signals have intensities which change depending on the longitudinal magnetization recovering through T1 relaxation after application of a 180-degree IR pulse. As a result, plot data $I_{abs}$, which are absolute values of the image signals, are plotted along a curve which is similar to a discrete curve indicating absolute values of a recovery curve of the longitudinal magnetization. The plot data $I_{abs}$ of the image signals is shown as in FIG. 5, where the plot data presents a positive minimum value at a certain TI and also presents values which become larger as the TI becomes smaller and larger from the certain TI.

Accordingly, an optimum $TI_{opt}$ for the imaging is a TI obtained when the value of an image signal recovery curve $I_{curve}$ shown by a solid line corresponding to the recovery curve of the longitudinal magnetization becomes zero. Hence the image signal partly inverted onto the positive side by calculating the absolute values thereof should be returned to its original negative values. The signs of the real part of the complex image signal can be used to determine whether or not there are inversions in the polarity of the signal. However, in cases where the phase of the image signal is shifted, it is difficult to correctly determine the signs and the original polarities of the image signal.

With this consideration, the fitting section 41A is configured to calculate the phase φ of a stable image signal obtained when the signal intensity has been recovered fully through the T1 relaxation. For example, any image signal whose intensity becomes higher than a threshold Th can be subjected to the calculation of the phase φ. Incidentally, in order to improve the accuracy of calculation of the phase φ, it is desired that the image signal obtained responsively to the longest TI be an object for the calculation of the phase φ.

The fitting section 41A is also configured to correct the phase of the image signal using the calculated phase φ. Practically the image signal obtained every TI is multiplied by exp(−jφ), whereby an image signal whose phase has been corrected is obtained. Next, image signal values whose real parts represent negative signs after the phase correction are plotted in the negative side area of the graph. This provides discrete corrected data $I_{cor}$ which can be plotted by a solid line marking in FIG. 5, where the polarities of the plotted data are corrected. As a result, there are provided discrete data with no singular point, which consist of the corrected plotted data $I_{cor}$ whose polarities are inverted and the plotted data $I_{abs}$ whose polarities are not inverted. This discrete data can be obtained as a plurality of image signals whose polarities have been corrected.

Next, the discrete data is subjected to curve fitting based on a least-square approach with the use of recovery curves with T1 values given as a parameter. By this fitting, from the discrete data, a formula defining the image signal recovery curve $I_{curve}$, whose data is continuous, is calculated. A TI value obtained when the value of the image signal recovery curve $I_{curve}$ is zero can thus be obtained accurately as the optimum $TI_{opt}$.

In this way, the phase correction is performed on a plurality of absolute-value image signals obtained responsively to a plurality of TI values, and the polarity correction is performed on the plurality of phase-corrected absolute-value image signals. The plurality of polarity-corrected phase-corrected absolute-value image signals can be subjected to the curve fitting. The optimum $TI_{opt}$ can thus be given as a TI value obtained when the value of a curve obtained by the curve fitting becomes zero.

Alternatively the curve fitting may be performed using curves of discrete absolute-value image signals. In this fitting, though calculating formulae are complicated, the phase correction process and polarity inversion process are not required.

Still alternatively, without performing the phase correction process, the absolute-value image signals can be used to calculate the optimum $TI_{opt}$ easily.

Figure 6:
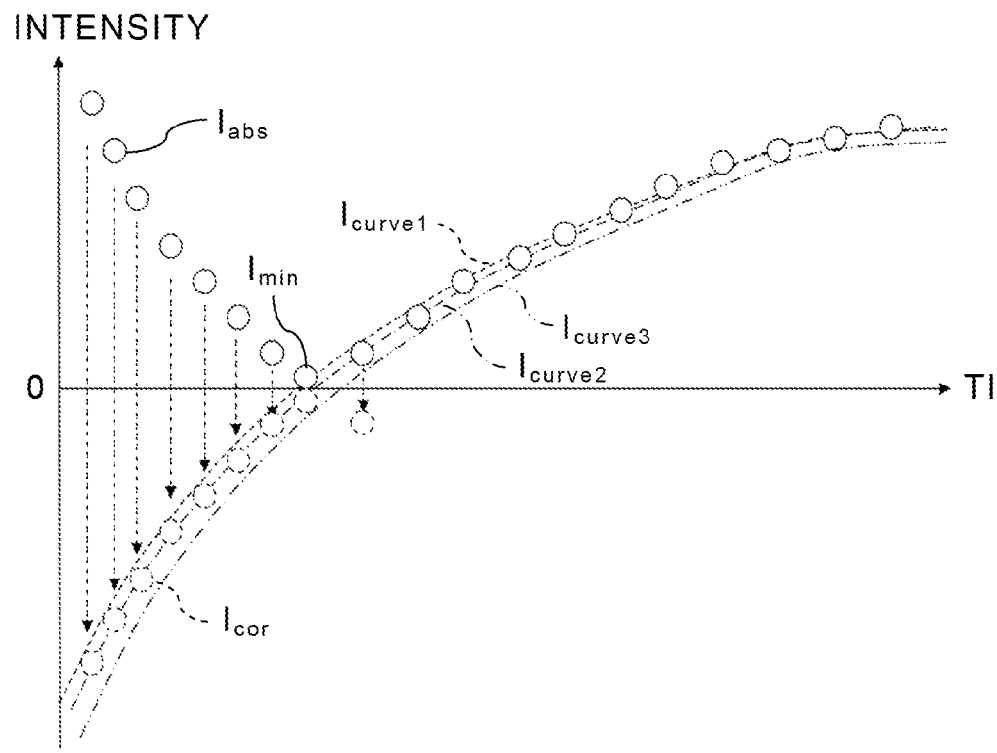
FIG. 6 is another graph explaining how to decide a $TI_{opt}$ for the imaging scan, which is performed by the data processing unit shown in FIG. 2.

FIG. 6 is a graph explaining the second decision technique for the $TI_{opt}$ for the imaging scan, which is performed by the data processing unit 41 shown in FIG. 2.

The graph in FIG. 6 has a vertical axis showing intensity of an image signal and a horizontal axis showing the TIs. As described above, a signal intensity is plotted every TI, which is obtained in a ROI in each of the plurality of sets of imaged data acquired through the pre-scan, which thus provides discrete absolute-value plotted data $I_{abs}$ as shown by a solid line marking.

A minimum value $I_{min}$ of the discrete plotted data $I_{abs}$ is then obtained. All of the polarities of absolute-value plotted data $I_{abs}$ whose TI values are shorter than a TI providing the minimum value $I_{min}$ are turned to the negative value, before the curve fitting using the least-square approach. This curve fitting calculation can provide a formula defining a first image signal recovery curve $I_{curve1}$ whose data are continuous as shown by a dashed line.

Next, the polarity of the minimum value Imin is turned to the negative value, and the curve fitting is performed on the curve using the least-square approach. This curve fitting calculation can provide a formula defining a second image signal recovery curve $I_{curve2}$ whose data is also continuous as shown by a dashed-dotted line.

Of the first and second image signal recovery curves $I_{curve1}$ and $I_{curve2}$, the curve whose degree of curve-fitted approximation is better than the other is adopted as a curve to calculate the $TI_{opt}$ for the imaging. An index indicating the degree of curve-fitted approximation can be, for example, an error sum of squares between the discrete data and the recovery curve. Concretely, either the first or second image signal recovery curve $I_{curve1}$ or $I_{curve2}$, which produces a smaller error sum of squares between each of the curves and the respective discrete data used to obtain those curves, is decided as an image signal recovery curve $I_{curve}$ to calculate the $TI_{opt}$ for imaging. It is thus possible to calculate, as the $TI_{opt}$ for imaging, a TI obtained when the image signal recovery curve $I_{curve}$ has a value of zero.

In this way, the first image signal recovery curve $I_{curve1}$ is obtained through the curve fitting performed on the first plural image signals obtained by inverting the respective polarities of the absolute-value image signals acquired responsively to a TI which is shorter than the TI corresponding to the minimum value $I_{min}$ of the plurality of absolute-value image signals acquired based on the plurality of TIs. Meanwhile the second image signal recovery curve $I_{curve2}$ is obtained through the curve fitting performed on the second plural image signals obtained by inverting both of the polarities of the absolute-value image signals acquired responsively to the minimum value $I_{min}$ and the absolute-value image signals acquired responsively to the TI which is shorter than the TI corresponding to the minimum value $I_{min}$. Then, in this second method, either one of the curves, which is superior to the other in the degree of approximation of the curve fitting, is adopted. This adoption makes it possible to easily calculate the image signal recovery curve $I_{curve}$ and a TI given when the image signal recovery curve $I_{curve}$ has a value of zero.

Alternatively, the curve fitting may be performed on data obtained by inverting, to the negative value side, the polarity of absolute-value plotted data $I_{abs}$, which are present in a TI range adjacent to but longer in the TI than the minimum value Imin among the discrete plotted data Iabs. In this case, as shown in FIG. 6, the formula defining a third image signal recovery curve $I_{curve3}$, which is shown by a two-dot chain line, is calculated as continuous data. Among the first, second and third image signal recovery lines $I_{curve1}$, $I_{curve2}$ and $I_{curve3}$, an image signal recovery curve which is best with regard to the degree of approximation of the curve fitting is adopted to calculate a $TI_{opt}$ for imaging. Obtaining the third image signal recovery line $I_{curve3}$ allows the processing to be robust even if data fluctuates due to some causes such as patient's breath.

In other words, in the first decision technique for the imaging $TI_{opt}$, absolute-value discrete data which should be inverted to the negative values thereof are decided through the phase correction, because a true minimum value of the image signal recovery curve $I_{curve}$ is unknown. By contrast, in the second decision technique, absolute-value discrete data which should be inverted to the negative values thereof are decided through comparison of an error of the curve fitting performed between a case where a minimum value of the discrete data, which are mapped around a true minimum value, and discrete data mapped adjacently to and from the minimum value are inverted and a case where those discrete data are not inverted.

In the second decision technique, without performing the complex phase correction processing, a reliable signal recovery curve and a $TI_{opt}$ for imaging which is a zero-crossing point of the signal recovery curve can be obtained. Moreover, in this second decision technique, when the third image signal recovery curve $I_{curve3}$ is not calculated, the data processing can be simplified more.

By the way, since the signal recovery curve is decided using the curve fitting, it is sufficient that, from a theoretical point of view, the pre-scan is performed to acquire image data depending on, at least, three TIs. Hence duration of the pre-scan can be shorter than the conventional. On the other hand, in order to obtain a $TI_{opt}$ for imaging at a practical precision, it is necessary to acquire image data, depending on a sufficient number of TIs, from, at least, a range estimated such that there is a zero-crossing point in the range.

Further, the image signal recovery curve $I_{curve}$ and the $TI_{opt}$ for imaging are calculated every ROI. This means that, on account of differences of components of myocardial tissue and densities of a contrast agent in the ROIs, the image signal recovery curve $I_{curve}$ and the $TI_{opt}$ for imaging might differ from each other among the ROIs. In such a situation, however, the TI which is set for imaging is only one TI.

Considering this, by way of example, an average value over the values $TI_{opt}$ for imaging at ROIs can be added to imaging conditions for imaging. Alternatively, of plural values $TI_{opt}$ obtained from a plurality of ROIs, the longest TI can be added to imaging conditions for imaging. Particularly, when the delayed enhancement is performed using a TI shorter than a TI corresponding to a zero-crossing point on a signal recovery curve obtained from the myocardial tissue, it is known that artifacts appear as black lines on the myocardial tissue. For the delayed enhancement, it is therefore effective against suppressing artifacts to add the longest TI to imaging conditions for imaging.

Hence, the fitting section 41A has functions of calculating a plurality of values $TI_{opt}$ obtained when the values of a plurality of image signal recovery curves $I_{curve}$ coming from a plurality of ROIs become zero, respectively, and adopting, as the TI for imaging, the longest $TI_{opt}$ among a plurality of values $TI_{opt}$ obtained from the plurality of ROIs.

The substance specifying information acquiring section 41B has a function of making the display unit 34 display the value of T1 obtained during performance of the curve fitting to calculate a $TI_{opt}$ for imaging, the value of the $TI_{opt}$, and the shape of an image signal recovery curve $I_{curve}$. In addition, as need arises, the substance specifying information acquiring section 41B is configured to calculate the value of a T1 through the curve fitting applied to discrete image data acquired at a desired ROI, the value of a $TI_{opt}$, and the shape of an image signal recover curve $I_{curve}$, and allow the display unit 34 to display information showing estimation or specification of a substance which is present at the ROI on the basis of at least one of the calculated value of the T1, the calculated value of the $TI_{opt}$, and the calculated shape of the image signal recovery curve $I_{curve}$. Practically, the substance specifying information acquiring section 41B has a function of allowing the display unit 34 to display at least one of the T1 value obtained using the curve fitting, the TI obtained when the image signal recovery curve $I_{curve}$ presents a value of zero, the shape of the image signal recovery curve $I_{curve}$, and information indicative of a substance estimated based on the T1 value.

The T1 and $TI_{opt}$ have values depending on components of a substance which is present in a ROI. Hence, by making the display unit 34 display bits of information which depend on the T1 value, which include the T1 value, the $TI_{opt}$ value, and the shape of the image signal recovery curve $I_{curve}$, a user can estimate the components of the substance which is present in the ROI. In addition, parallel display of the shapes of image signal recovery curves $I_{curve}$ resulting from a plurality of ROIs makes it possible that a user uses differences among the shapes of the image signal recovery curves $I_{curve}$ to confirm that there are substance components in a specific ROI which are different from those in the other ROIs.

For example, in the cardiac delayed enhancement, it is possible to specify which of blood, cardiac infarction area, and contrast agent composes an essential substance component in a ROI. Hence, in addition to ROIs for calculating a $TI_{opt}$ for imaging, a ROI can be placed at areas of interest, such as a suspected area as a site of lesion, to calculate information depending on the T1 value and allow the display unit 34 to display the calculated information. As an alternative, the T1 value and the name itself of a substance, such as blood, cardiac infarction area or contrast agent, which is estimated based on the $TI_{opt}$ value, can be displayed on the display unit 34 as information indicative of estimation or specification of the substance.

As a result of these display approaches, a user can make judgments on various cases, such as a case where it is needed to judge which of artifacts or lesional tissue gives higher-intensity signals to an area which is suspected as an area of lesion.

The image producing section 41C also has various functions, which include a function of producing image data by applying a image reconstruction process and some other necessary image processes, a function of writing the produced image data in the image data storage section 43, and a function for display. The image reconstruction process includes Fourier transform (FT) applied to k-space data acquired by a pre-scan and an imaging scan. The display function allows the image data to be read from the image data storage section 43, to undergo necessary image processing, and to be displayed on the display unit 34.

For example, the image processing includes, in addition to setting a ROI for calculating the $TI_{opt}$ for imaging, a phase correction process and a calculation process of the image signal recovery curve $I_{curve}$ by curve fitting, both processes of which are applied to the entire region or a desired region of a region composed of image data.

The operations and functions of the magnetic resonance imaging apparatus 20 will now be described.

Figure 7:
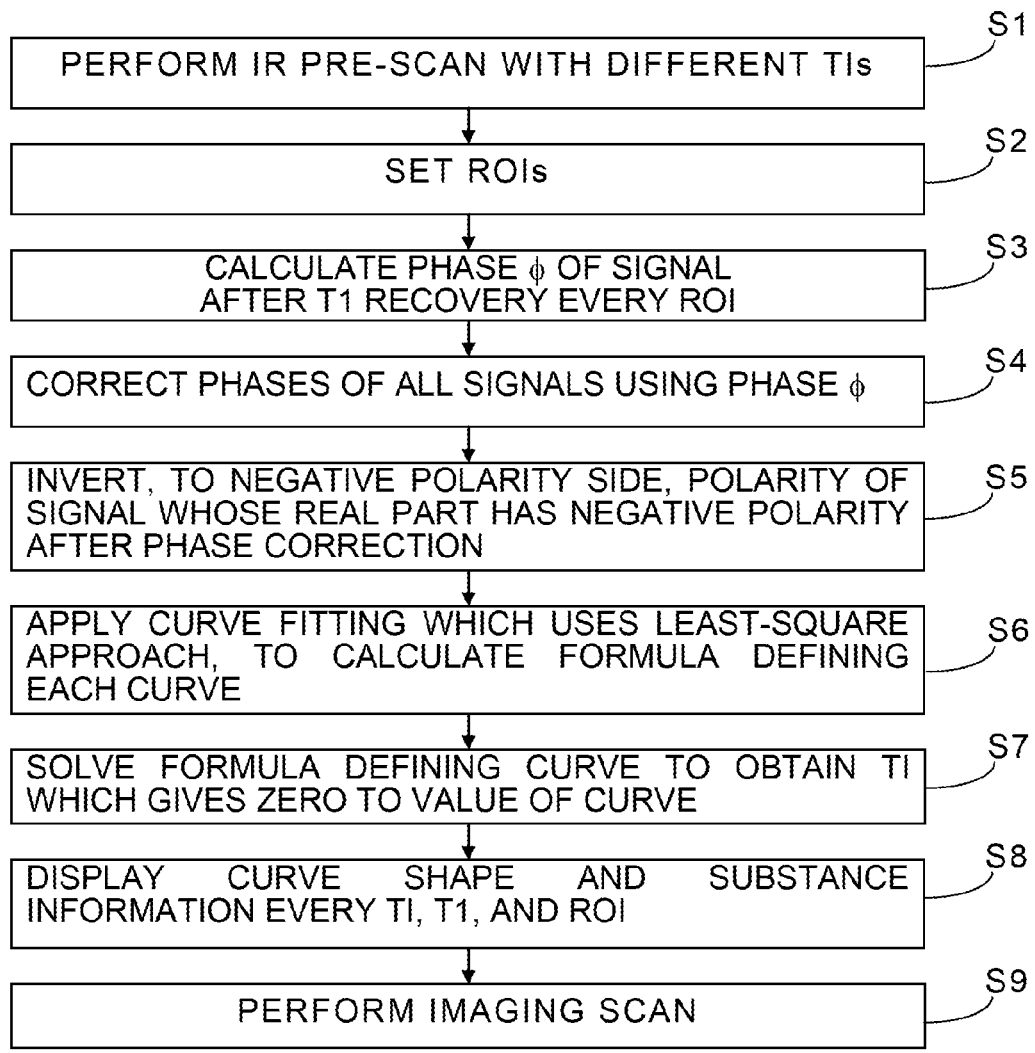
FIG. 7 is a flowchart showing a flow along which the magnetic resonance imaging apparatus shown in FIG. 20 performs imaging based on the IR method.

FIG. 7 is a flowchart of imaging based on the IR method, which is performed by the magnetic resonance imaging apparatus 20 shown in FIG. 1. This flowchart exemplifies a case where the $TI_{opt}$ for imaging scan is decided through the first decision technique involving the phase correction shown in FIG. 5.

An object P is first set on the bed 37 in advance, and the static magnetic field power supply 26 is activated to drive the static field magnet 21 (i.e., superconductive magnet) such that a static magnetic field is produced in an imaging region of the static field magnet 21. The shim coil 22 is also driven by current from the shim coil power supply 28 so that the static magnetic field produced in the imaging region becomes uniform.

At step S1, with the TI values changed, the IR pre-scan is performed to acquire a plurality of frames of image data. Practically, the multi-TI setting section 40A sets plural TI values which are different from each other, and the IR sequence setting section 40B uses the plural TI values to set an IR sequence for the pre-scan. As a result, as shown in (A) of FIG. 3, the IR sequence is set as an imaging condition for the pre-scan, where the IR sequence has different TI values for acquiring data in synchronization with an R-wave in the ECG signal.

The imaging condition setting unit 40 then provides the sequence controller 31 with imaging conditions for the pre-scan, which imaging conditions include the IR sequence. In response to this, the sequence controller 31 activates the gradient power supply 27, the transmitter 29, and the receiver 30 according to the imaging conditions, resulting in the production of gradient magnetic fields in the imaging region in which the object P is located and the generation of RF signals from the RF coils 24.

Hence, MR signals caused by the nuclear magnetic resonance within the object P are received by the RF coils 24 and then sent to the receiver 30. The receiver 30 receives the MR signals from the RF coils 24 to produce digital-format raw data from the MR signals. The receiver 30 provides the sequence controller 31 with the produced MR data, and, in response to this, the sequence controller 31 outputs the MR data to the data processing unit 41. As a result, the data processing unit 41 maps, as k-space data, the MR data in the k-space virtually formed in the k-space data storage section 42.

Then, the image producing section 41C performs with the k-space data acquired by the pre-scan, so that image data are produced. In this production, a plurality of frames of image data respectively responding to the plurality of TIs are produced. The produced image data are displayed on the display unit 34.

Then at step S2, in response to information from the input device 33 manipulated by the user, the fitting section 41A places ROIs on the displayed image data acquired through the pre-scan. For example, as shown in FIG. 4, a plurality of ROIs are set.

Then at step S3, the fitting section 41A computes, every ROI, the phase $\phi$ of a complex absolute-value image signal depending on a TI at which the T1 relaxation recovery of the image signal has been sufficient. Whether or not the T1 relaxation recovery is sufficient can be checked by the T1 relaxation recovery becomes over a threshold Th which is set as shown in FIG. 5.

Then at step S4, the fitting section 41A uses the computed phase $\phi$ to correct the phases of the complex absolute-value image signals acquired depending on all the TIs.

Then at step S5, the fitting section 41A determines whether or not the polarity of each real part of the complex absolute-value image signals whose phases have been corrected is negative. When this determination reveals that the polarity is negative, the polarity of each complex absolute-value image signal is inverted to the negative side as shown in FIG. 5.

Then at step S6, the fitting section 41A applies a curve fitting technique to the polarity-corrected image signal responding to the plurality of discrete TIs so as to calculate the formula of an image signal recovery curve $T_{curve}$ as shown in FIG. 5. The curve fitting technique is performed based on the least-square approach.

Then at step S7, the fitting section 41A calculates a $TI_{opt}$ given when the formula of the image signal recovery curve $I_{curve}$ presents a value of zero. This calculation is conducted to provide the $TI_{opt}$ every ROI. The fitting section 41A then obtains, as a $TI_{opt}$ for imaging, an average of $TI_{opt}$ values or the longest one of $TI_{opt}$ values in all the ROI.

Then at step S8, the substance specifying information acquiring section 41B allows the display unit 34 to display the value of the T1 obtained through the curve fitting, the value of the $TI_{opt}$, and the shape of the image signal recovery curve $I_{curve}$. In cases where the user inputs information specifying a new ROI by manipulating the input device 33, the substance specifying information acquiring section 41B also acquires the value of a T1, the value of a $TI_{opt}$, and the shape of an image signal recovery curve $I_{curve}$ through a curve fitting process applied to image data designated by the newly set ROI.

Further, the substance specifying information acquiring section 41B allows the display unit 34 to display thereon the T1 value, the $TI_{opt}$ value, and bits of information which depend on the T1 value, such as a shape of image signal recover curve $I_{curve}$ as well as information indicative of estimation or specification of a substance, which is estimated on the information depending on the T1 value. In this way, the user can estimate essential components of substances which are present within the ROI. Additionally, the user can check the value of the $TI_{opt}$ calculated as an analysis performed by the fitting section 41A. Moreover, as need arises, the ROI can be re-set and the TIopt can be re-calculated.

Then at step S9, the components for imaging implemented in the magnetic resonance imaging apparatus 20 performs imaging based on the IR method using the $TI_{opt}$ calculated for the imaging. Concretely, the IR sequence setting section 40B will set, as one of imaging conditions for an imaging scan, an IR sequence to acquire data at the $TI_{opt}$ in synchronism with an R-wave in the ECG signal as shown in (B) of FIG. 3. Similarly to the same flow as that of the pre-scan, the imaging scan is performed.

The imaging producing section 41C then produces image data for diagnosis by applying an image reconstruction process and necessary various processes to the k-space data acquired by the imaging scan. This diagnostic image data are produced based on the optimum inversion time $TI_{opt}$.

When a diagnostic image is a cardiac delay-enhanced image, the IR imaging is performed at the optimum inversion time $TI_{opt}$ which is set to suppress signals from the normal myocardial tissue. As a result, if there are areas of cardiac infarction, those areas can be depicted more clearly as higher signal intensity portions. It is therefore possible that users can easily understand whether or not there is an area of cardiac infarction and/or the position of the area of infarction if there is such an area.

In this way, the magnetic resonance imaging apparatus 20 acquires image data with different inversion times TI changed according to the IR method. This apparatus further performs the imaging scan using, as one of the imaging conditions, an inversion time TI obtained when a signal recovery curve presents a value of zero, where the curve is provided by applying curve fitting to image signals for each inversion time TI.

Hence, in the magnetic resonance imaging apparatus 20, the IR imaging such as delay enhancement can be performed, where a more optimum inversion time TI can be provided more easily and accurately. This results in obtaining higher-quality image data. In particular, in this magnetic resonance imaging apparatus 20, the inversion time TI is set analytically based on the formula of a continuous signal recovery curve. Compared with the conventional method of setting the inversion time TI based on visual observation of an absolute-value image, erroneous recognition of a minimum value of image signals can be reduced. This will lead to reducing failure of imaging scans, retry of a pre-scan, and/or poor depiction of image data.

Second Embodiment

Figure 8:
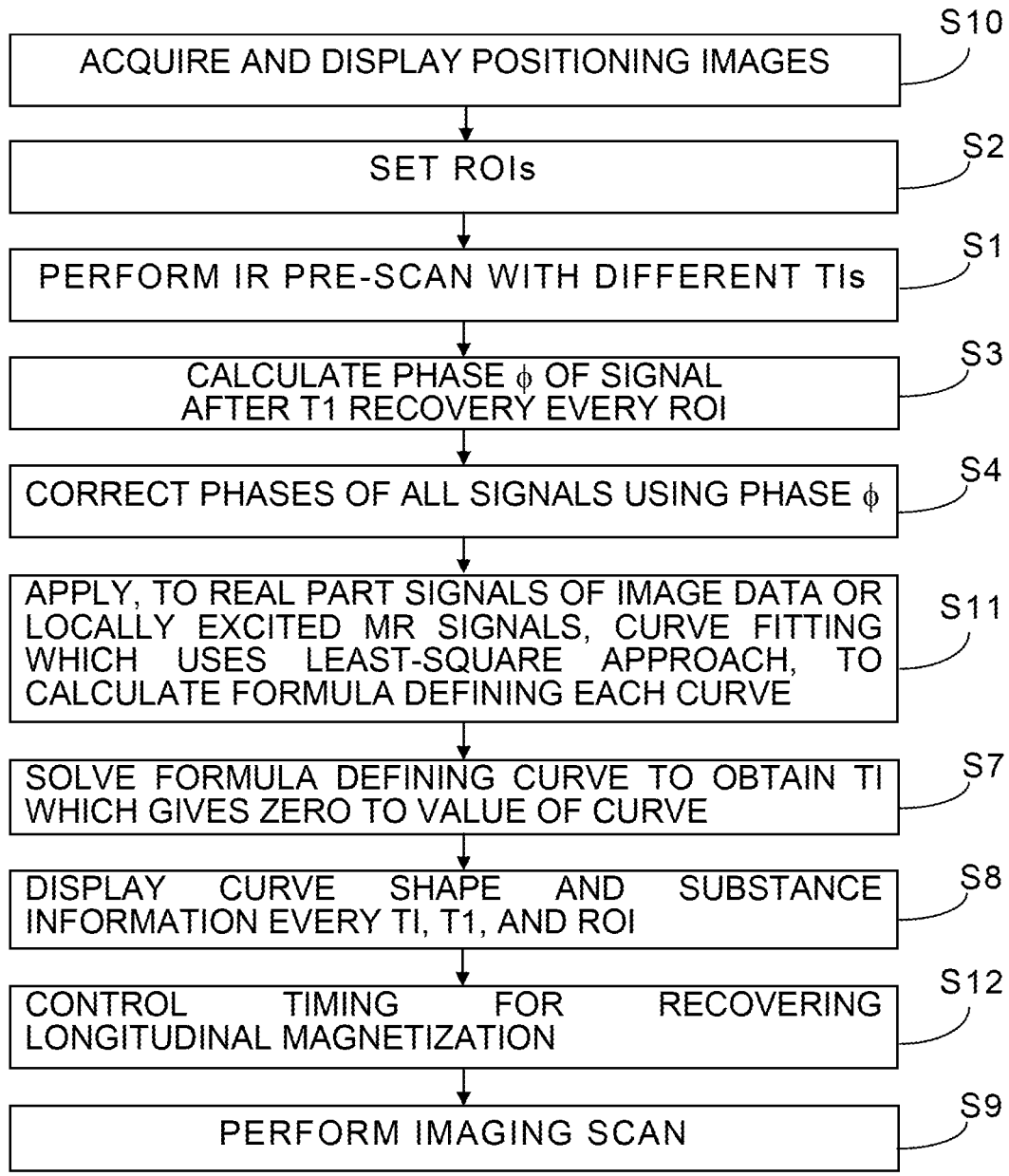
FIG. 8 is a flowchart showing a flow along which a magnetic resonance imaging apparatus according to the second embodiment of the present invention performs imaging.

FIG. 8 is a flowchart showing the flow of imaging performed by a magnetic resonance imaging apparatus according to a second embodiment of the present invention.

In the magnetic resonance imaging apparatus according to the second embodiment, a ROI is set prior to performing a pre-scan. Because of this, this imaging apparatus differs from the magnetic resonance imaging apparatus 20 according to the first embodiment in that an imaging scan can be performed continuously from the pre-scan. In addition, differently from the apparatus 20 according to the first embodiment, the apparatus of the present embodiment employs curve fitting which is performed using real part signals of MR signals and image signals. Hence, details of functions of components realizing the above features also differ from those of the first embodiment. The configurations and functions of other components of the magnetic resonance imaging apparatus according to the second embodiment are similar to those in the apparatus 20 described in the first embodiment. Accordingly, only a flowchart is shown in the second embodiment, and the components and flowchart steps which are similar or the same to or as those in the first embodiment are given the same references for the sake of simplified or omitted description.

Practically, the imaging components of the magnetic resonance imaging apparatus according to the second embodiment performs mutually continuously both acquisition of a plurality of image data or a plurality of MR signals responding to a plurality of inversion times TI and imaging.

For realizing such continuous functions, at step S10, positioning image data for setting ROIs are acquired in a manner similar to an imaging scan. The acquired positioning image is displayed on the display unit 34.

Then at step S2, the imaging condition setting unit 40 uses the positioning image to set ROIs thereon. The ROIs, which are set here, function as areas from which data for curve fitting are acquired. Thus, under displaying as the positioning image a morphological image along a section of the heart, the input device 33 is manipulated to place one or more ROIs on the myocardial tissue.

Then at step S1, an IR pre-scan is performed to acquire image data for a plurality of frames with the inversion time TI changed to various durations. In this stage, the ROIs to acquire data for the curve fitting have already been set. Hence, instead of MR signals for producing image data, MR signals may be acquired from the areas defined by the ROIs. In this case, local excitation in the ROIs enables acquisition of MR signals.

Then at step S3, the fitting section 41A calculates, for every ROI, the phases φ of the image signals or the MR signals whose T1 relaxation has been recovered fully. However, the phases which are calculated here are not those of the complex absolute-value image signals, but the phases φ of complex image signals or complex MR signals each having real and imaginary parts.

Then at step S4, the fitting section 41A uses all the calculated phases φ to correct the phases of complex image signals or complex MR signals acquired through the local excitation, which complex image or MR signals are acquired responding to all the inversion times TI and from the areas defined by the ROIs. As a result of this phase correction, image signals or MR signals whose imaginary-part signals are zero and real-part signals have values can be obtained.

Then at step S11, the fitting section 41A applies curve fitting to the real-part signals of the image signals or the real-part signals of the locally excited MR signals, whose phases have already been corrected, using the least-square approach. By this processing, there is provided the formula of a recovery curve of the image signals or the MR signals indicating the T1 relaxation at areas such as myocardium.

Then at step S7, the fitting section 41A calculates, as the inversion time TI for imaging, an inversion time TI which allows the formula of the recovery curve of the image or MR signals to have an amount of zero. In addition, at step S8, if need arises, the substance specifying information acquiring section 41B makes the display unit 34 display information indicating estimation or specification of a substance, which is estimated based on information including the longitudinal relaxation T1 and inversion time TI obtained through the curve fitting.

Then at step S12, the imaging condition setting unit 40 controls the sequence controller 31 such that the imaging scan is started automatically at a time when the longitudinal magnetization inverted by the IR pre-scan has recovered sufficiently. Hence, the magnetic resonance imaging performs its stand-by operation in cases where it will take a long time to achieve a sufficient recovery of the longitudinal magnetization.

In acquiring data under the general IR method, the IR pulse is applied several times before the data acquisition so that the inverted longitudinal magnetization recovers up to a given level during an interval between R-waves of the ECG signal. In other words, application of the IR pulse not involving data acquisition, which is called blind application, makes it possible to previously adjust a recovery amount of the longitudinal magnetization at a reference timing such as a R-wave. In the IR pre-scan, this blind application can be performed to adjust a recovery amount of the longitudinal magnetization between R-waves.

For this adjustment, the imaging condition setting unit 40 provides the sequence controller 31 with information for commanding the execution of an imaging sequence at a time when a sufficient recovery amount of the longitudinal magnetization, which can start an imaging scan, is expected. This scan timing can be controlled based on, for example, an elapsed time from at a time when the IR pulse is applied in the IR pre-scan and the T1 value.

There can also be provided an alternative timing control method of making the longitudinal magnetization recover up to a proper level in acquiring imaging data. This alternative method is to give the same value to both repetition times TR of the IR pre-scan and the imaging scan. Practically, when the interval of R-wave of the ECG signal is denoted by "RR," the repetition time TR of the imaging scan is set to "1RR" and "2RR" when the repletion time TR of the IR pre-scan is "1RR" and "2RR," respectively, for example. Therefore, the recovery amount of the longitudinal magnetization can be adjusted to the same amount in performing the IR pre-scan and the imaging scan.

In this case, the input device 33 is allowed to provide the imaging condition setting unit 40 with information indicating both repetition times TR for the IR pre-scan and imaging scan. This enables both repetition times TR in the pre-scan and imaging scan can be set to the same amount. Alternatively, when one of the repetition times TR for the IR pre-scan and imaging scan is given from the input device 33 to the imaging condition setting unit 40, this unit 40 can operate to automatically set the other repetition time TR to the same amount as that given from the input device 33.

When the repetition times TR for the IR pre-scan and imaging scan is set to 1RR or 2RR and the inversion time TI is computed at a high speed at step S7, the timing can be controlled to enable the imaging scan to be performed using, as a trigger, an R-wave appearing immediately after the IR pre-scan. Since the longitudinal magnetization cannot recover so much at the stage immediately after the IR pre-scan, the imaging scan can be performed continuously.

In contrast, when it takes a certain time to calculate the inversion time TI, the timing is controlled to allow the imaging scan to start using, as the trigger, an R-wave appearing at a time elapsing by a given period of time after the IR pre-scan. In this case, the foregoing blind application is also performed before performing the imaging scan to prevent the longitudinal magnetization cannot from recovering too much after performing the IR pre-scan. The repetition times TR of the pre-scan and imaging scan are set to the same amount. Hence, thanks to these procedures, it is possible to make levels of the longitudinal magnetization equal to each other in the data acquisition. That is, depending on conditions such as calculated values of the inversion time TI, the blind application can be performed prior to the imaging scan. The conditions necessary in setting the longitudinal magnetization for starting the imaging scan can be given in a favorable manner.

On completion of sufficient recovery of the longitudinal magnetization, a process is executed at step S9, where the imaging scan is started automatically. Practically, the imaging condition setting unit 40 provides the sequence controller 31 with not only imaging conditions including the inversion time TI calculated for the imaging but also information, as control information, indicating a command of start of the imaging scan. This enables the imaging scan to be performed based on the IR method with the optimally set inversion time TI, with MR signals acquired and MR image data produced accordingly.

Thus, in the magnetic resonance imaging apparatus according to the second embodiment, the imaging scan can be executed continuously after the IR pre-scan. It is therefore possible to shorten the imaging time and reduce an amount of user's operations.

Additionally, the local excitation permits the data processing unit 41 to analyze a plurality of MR signals respectively responding to a plurality of inversion times TI, without being limited to analyze image data, in order to calculate an inversion time TI. In other words, the fitting section 41A can calculate, as the imaging inversion time TI, an inversion time TI obtained when a curve shows a value of zero, which curve results from the curve fitting applied to the plurality of image data or the plurality of MR signals respectively responding to the plurality of inversion times TI.

Still additionally, the fitting section 41A can perform the curve fitting by using, in place of absolute-value image signals, real-part signals of either a plurality of phase-corrected image data responding to a plurality of inversion times TI or a plurality of phase-corrected MR signals responding to a plurality of inversion times TI and being acquired by local excitation. This eliminates the need for inverting the polarities shown in FIG. 5 or step S5 in FIG. 7.

Incidentally, in the first embodiment, instead of using the absolute-value image signals, the curve fitting can be performed using the real parts of complex image signals whose phases have been corrected. In this first embodiment, the inversion of the polarities cannot be required. Conversely, in the first embodiment where the curve fitting is performed on the absolute-value image signals shown in FIGS. 5 and 6, the imaging scan can be executed continuously from the performance of the IR pre-scan.

Other Embodiments

As described, while certain embodiments of the inventions have been described, these embodiments have been presented by way of example only, and are not intended to limit the scope of the inventions. Indeed, the novel methods and systems described herein may be embodied in a variety of other forms; furthermore, various omissions, substitutes and changes in the form of the methods and systems described herein may be made without departing from the spirit of the inventions. The accompanying claims and their equivalents are intended to cover such forms or modifications as would fall within the scope and spirit of the inventions.

What is claimed is:

1. A magnetic resonance imaging apparatus comprising:
a calculation unit configured to provide a calculated inversion time for an imaging scan by analyzing frames of image data or magnetic resonance signals acquired from an object, the frames being acquired in response to a plurality of inversion times which are different from each other; and
an imaging unit configured to perform the imaging scan using the calculated inversion time,
wherein the calculation unit is further configured to
calculate, using the frames, a phase based on the image data or the magnetic resonance signal corresponding to a first inversion time,
perform phase correction of the image data or the magnetic resonance signal corresponding to a second inversion time, the phase correction being performed using the calculated phase, and
determine the calculated inversion time based on a curve obtained by applying curve fitting to the frames after performing the phase correction.

2. A magnetic resonance imaging apparatus of claim 1, wherein said calculation unit is further configured to determine the calculated inversion time as the inversion time for the imaging which is given when the curve becomes zero.

3. A magnetic resonance imaging apparatus of claim 1, further comprising
a substance specifying unit configured to enable a display unit to display at least one of a T1 value obtained through the curve fitting, the inversion time given when the curve becomes zero, a shape of the curve, and information indicating a substance estimated based on the T1 value.

4. A magnetic resonance imaging apparatus of claim 1, wherein said imaging unit is configured to perform cardiac delayed enhancement imaging or non-enhancement blood flow imaging.

5. A magnetic resonance imaging apparatus of claim 2, wherein said calculation unit is further configured to determine a plurality of inversion times corresponding to when values of curves fitted to image data or magnetic resonance signal in regions of interest become zero respectively and to adopt a longest inversion time out of the plurality of inversion times as the calculated inversion time for the imaging.

6. A magnetic resonance imaging apparatus of claim 2, wherein said imaging unit is configured to sequentially perform both the imaging and acquisition of the frames obtained in response to the inversion times.

7. A magnetic resonance imaging apparatus of claim 2, wherein said calculation unit is further configured to perform the curve fitting by using real-part signals of frames of image data obtained after the phase correction and corresponding to the inversion times or real-part signals of magnetic resonance signals obtained through local excitation, after the phase correction, and corresponding to the inversion times.

8. A magnetic resonance imaging apparatus of claim 2, wherein said calculation unit is further configured to perform the phase correction with absolute-value image signals corresponding to the inversion times to perform the curve fitting using image signals obtained by correcting polarities of absolute-value image signals obtained after the phase correction.

9. A magnetic resonance imaging apparatus comprising:
a calculation unit configured to provide a calculated inversion time for an imaging scan by analyzing frames of image data acquired from an object, the frames being acquired in response to inversion times which are different with each other; and an imaging unit configured to perform the imaging scan using the calculated inversion time, wherein the calculation unit is further configured to obtain a first curve by the curve fitting with first image signals obtained by inverting polarities of absolute-value image signals each acquired in response to an inversion time shorter than an inversion time corresponding to a minimum value of absolute-value image signals acquired in response to the inversion times, obtain a second curve by the curve fitting with second image signals obtained by inverting a polarity of an absolute-value image signal corresponding to the minimum value and respective polarities of the absolute value image signals each obtained responsive to the inversion time shorter than the inversion time corresponding to the minimum value, and determine the calculated inversion time from a curve adopted based on a degree of approximation of the curve fitting.

10. A magnetic resonance imaging apparatus comprising:

a calculation unit configured to calculate a formula of a curve obtained by curve fitting applied to frames of image data or magnetic resonance signals acquired responsively to inversion times which are different with each other and set based on a recovery method; and a substance specifying unit configured to enable a display unit to display at least one of a T1 value obtained through the curve fitting, the inversion time given when the curve becomes zero, a shape of the curve, and information indicating a substance estimated based on the T1 value.

11. A magnetic resonance imaging method comprising:

determining a calculated inversion time for an imaging scan by analyzing frames of image data or magnetic resonance signals acquired from an object, the frames being acquired in response to inversion times which are different with each other; and performing the imaging scan using the calculated inversion time, wherein the determining a calculated inversion time comprises:

calculating, using the frames, a phase based on the image data or the magnetic resonance signals corresponding to a first inversion time, performing phase correction of image data or magnetic resonance signal corresponding to a second inversion time using the phase, and determining the calculated inversion time based on a curve obtained by applying curve fitting to the frames of the image data after the phase correction or the magnetic resonance signals after the phase correction.

* * * * *